(12) United States Patent
Shalaby et al.

(10) Patent No.: US 8,986,393 B2
(45) Date of Patent: *Mar. 24, 2015

(54) RADIATION AND RADIOCHEMICALLY STERILIZED FIBER-REINFORCED, COMPOSITE URINOGENITAL STENTS

(75) Inventors: Shalaby W. Shalaby, Anderson, SC (US); Kenneth W. Clinkscales, Easley, SC (US); Kenneth D. Gray, Clemson, SC (US)

(73) Assignee: Poly-Med, Inc., Anderson, SC (US)

( * ) Notice: Subject to any disclaimer, the term of this patent is extended or adjusted under 35 U.S.C. 154(b) by 190 days.

This patent is subject to a terminal disclaimer.

(21) Appl. No.: 13/301,894

(22) Filed: Nov. 22, 2011

(65) Prior Publication Data

US 2012/0083897 A1   Apr. 5, 2012

Related U.S. Application Data

(63) Continuation of application No. 12/378,221, filed on Feb. 12, 2009, now Pat. No. 8,083,806, which is a continuation-in-part of application No. 11/346,117, filed on Feb. 2, 2006, now Pat. No. 8,252,064, which is a continuation-in-part of application No. 11/204,822, filed on Aug. 16, 2005, now Pat. No. 8,083,805.

(60) Provisional application No. 60/650,240, filed on Feb. 4, 2005.

(51) Int. Cl.
| | |
|---|---|
| *A61F 2/04* | (2013.01) |
| *A61F 2/06* | (2013.01) |
| *A61L 31/12* | (2006.01) |
| *A61L 31/14* | (2006.01) |
| *A61L 31/16* | (2006.01) |
| *A61L 31/18* | (2006.01) |
| *A61M 27/00* | (2006.01) |

(Continued)

(52) U.S. Cl.
CPC ............. *A61L 31/129* (2013.01); *A61L 31/148* (2013.01); *A61L 31/16* (2013.01); *A61L 31/18* (2013.01); *A61M 27/008* (2013.01); *A61F 2/04* (2013.01); *A61F 2/94* (2013.01); *A61L 2300/404* (2013.01); *A61L 2300/416* (2013.01); *A61M 25/0108* (2013.01)
USPC ..... 623/23.66; 623/1.33; 623/1.34; 623/1.38; 623/1.49; 623/1.5; 623/1.54; 623/23.7

(58) Field of Classification Search
USPC ............. 623/1.32–1.34, 1.38, 1.45, 1.49–1.5, 623/1.54, 23.64–23.71
See application file for complete search history.

(56) References Cited

U.S. PATENT DOCUMENTS 5,052,998 A * 10/1991 Zimmon ............................ 604/8
5,085,629 A    2/1992 Goldberg et al.

(Continued)

FOREIGN PATENT DOCUMENTS

CA    2596885    8/2006
WO    WO0191668 A1    12/2001

OTHER PUBLICATIONS

Supplementary European Search Report dated May 13, 2013 from corresponding European Patent Application No. 10741503.

*Primary Examiner* — Andrew Iwamaye
(74) *Attorney, Agent, or Firm* — McNair Law Firm, P.A.; Douglas L. Lineberry

(57) ABSTRACT

A radiation and radiochemically sterilized, multi-component, fiber-reinforced composite, absorbable/disintegratable urinogenital stent, such as an endoureteral stent, with radiomodulated residence time in the biological site of 1 to 10 weeks depending on the high energy radiation dose used for sterilization.

3 Claims, 2 Drawing Sheets

(51) Int. Cl.
*A61F 2/94* (2013.01)
*A61M 25/01* (2006.01)

(56) References Cited

U.S. PATENT DOCUMENTS

| | | | |
|---|---|---|---|
| 5,449,382 A | 9/1995 | Dayton | |
| 6,017,362 A | 1/2000 | Lau | |
| 6,462,169 B1* | 10/2002 | Shalaby | 528/354 |
| 6,794,485 B2* | 9/2004 | Shalaby et al. | 528/354 |
| 7,465,489 B2* | 12/2008 | Shalaby et al. | 428/296.7 |
| 8,083,805 B2* | 12/2011 | Shalaby | 623/23.66 |
| 8,083,806 B2* | 12/2011 | Shalaby et al. | 623/23.66 |
| 8,252,064 B2* | 8/2012 | Shalaby et al. | 623/23.66 |
| 2001/0021873 A1* | 9/2001 | Stinson | 623/1.34 |
| 2002/0031601 A1* | 3/2002 | Darouiche et al. | 427/2.1 |
| 2002/0155159 A1* | 10/2002 | Shalaby | 424/486 |
| 2003/0069629 A1* | 4/2003 | Jadhav et al. | 623/1.15 |
| 2003/0120029 A1* | 6/2003 | Shalaby et al. | 528/310 |
| 2003/0162940 A1* | 8/2003 | Shalaby | 528/425 |
| 2003/0209835 A1 | 11/2003 | Chun et al. | |
| 2004/0109892 A1* | 6/2004 | Shalaby | 424/468 |
| 2004/0133237 A1 | 7/2004 | Shalaby | |
| 2004/0138644 A1 | 7/2004 | DiCarlo et al. | |
| 2004/0138738 A1* | 7/2004 | Stinson | 623/1.38 |
| 2004/0249441 A1* | 12/2004 | Miller et al. | 623/1.15 |
| 2006/0178739 A1* | 8/2006 | Shalaby et al. | 623/1.49 |
| 2007/0203564 A1 | 8/2007 | Rusk et al. | |

* cited by examiner

US 8,986,393 B2

RADIATION AND RADIOCHEMICALLY STERILIZED FIBER-REINFORCED, COMPOSITE URINOGENITAL STENTS

This application is a continuation application of U.S. Ser. No. 12/378,221, filed Feb. 12, 2009, now U.S. Pat. No. 8,083,806, which is a continuation-in-part of U.S. Ser. No. 11/346,117, filed Feb. 2, 2006, now U.S. Pat. No. 8,252,064 which is a continuation-in-part application of U.S. Ser. No. 11/204,822 filed Aug. 16, 2005, now U.S. Pat. No. 8,083,805, which claims the benefit of prior provisional application U.S. Ser. No. 60/650,240 filed Feb. 4, 2005.

FIELD OF THE INVENTION

This invention relates to patient-customized, non-migrating, fiber-reinforced, composite absorbable/disintegratable urinogenital stent that is radiochemically sterilized with about 3 to 15 kGy and radiation sterilized with 25 to 40 kGy of high-energy radiation to modulate its residence time in a typical urinogenital conduit such as a ureter in order to maintain optimum ureteral patency for predetermined periods of time between 1 and 10 weeks. At the conclusion of the specific predetermined period, the stent is expected to have practically no physical presence in the ureter that may interfere with pertinent biological functions.

BACKGROUND OF THE INVENTION

Most pertinent to this application are a number of aspects of the prior application of U.S. Ser. No. 11/346,117 which dealt with (1) an absorbable/disintegratable, multicomponent, non-migrating, endoureteral stent which is a tubular construct of a fiber-reinforced, elastomeric, tubular film designed with at least one position retaining end which can be in the form of a flexible, reversible loop or pigtail; and (2) fiber-reinforced stent wherein the fiber reinforcement is a combination of radiopaque monofilament coil made of an absorbable, segmented, polyaxial copolyester with barium sulfate microparticles dispersed therein and a weft-knitted mesh made of multifilament yarn derived from an absorbable, segmented, polyaxial copolyester. However, the prior application was silent on (1) relating the claimed composition of the construct component to definite residence time in a conduit such as the ureter; (2) addressing how to facilitate the insertion of the stent into a moist conduit tract, in part with the aid of a pusher and guide wire, without compromising the physical integrity of the stent; and (3) dealing with how to package and sterilize the stent and its complementary components, should ethylene oxide, the standard sterilization method for absorbable devices, is deemed less than optimum for use. The silence of the prior application on these clinically important aspects of a useful stent provided an incentive to pursue the study subject of this invention. Accordingly, this invention deals with a fiber-reinforced composite, absorbable/disintegratable, urinogenital stent that is radiochemically sterilized or radiation sterilized using the proper dose to modulate its residence time in a specific urinogenital conduit, such as a ureter, for a predetermined period of time ranging between 1 and 10 weeks.

SUMMARY OF THE INVENTION

A general aspect of the invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles, wherein the urinogenital conduit is selected from the group consisting of ureters, urethras, vas deferens, uterine tubes, fallopian tubes and ejaculatory ducts, and wherein the stent is in the form of a tube having a main central body and at least one position-retaining end comprising a flexible extension of the main central body, and having a loop shape with an open end parallel to the axis of the main central body after insertion in the urinogenital conduit wherein the loop can be made co-linear with the aid of an applicator. Additionally, the stent is in the form of an endoureteral stent having a diameter that is less than that of the urinogenital conduit and the matrix component comprises an absorbable, high molecular weight, low-crystallinity, segmented polyaxial copolyester exhibiting an inherent viscosity of from about 0.5 to about 2.0 dL/g and heat of fusion ([Delta]Hf) of from about 2 to about 30 J/g and derived from 1-lactide and at least one additional monomer selected from the group consisting of glycolide, trimethylene carbonate, [epsilon]-caprolactone, p-dioxanone, 1,5-dioxepan-2-one and a morpholinedione.

A key aspect of this invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles, wherein the matrix comprises an absorbable, segmented, polyaxial copolyester and a high molecular weight, hydrophilic polymeric additive having a molecular weight of about 1 to about 70 kDa, the additive selected from the group consisting of polyethylene glycol, and polyethylene glycol end-grafted with at least one monomer selected from the group consisting of 1-lactide, glycolide, trimethylene carbonate, [epsilon]-caprolactone, p-dioxanone, 1,5-dioxepan-2-one and a morpholinedione, and wherein the matrix comprises an absorbable polyether-ester comprising an aliphatic polyether glycol end-grafted with at least one monomer selected from the group consisting of 1-lactide, glycolide, trimethylene carbonate, [epsilon]-caprolactone, p-dioxanone, 1,5-dioxepan-2-one and a morpholinedione and having an inherent viscosity of from about 0.6 to about 1.8 dL/g and an overall heat of fusion ([Delta]Hf) of from about 5 to about 30 J/g, and further wherein the load-bearing radiopaque central reinforcing coil comprises a hybrid monofilament consisting of from about 30 to about 60 weight percent of barium sulfate microparticles dispersed in a crystalline high molecular segmented polyaxial copolyester exhibiting an inherent viscosity of from about 0.6 to about 2.0 dL/g and a heat of fusion ([Delta]Hf) of from about 20 to about 80 J/g, the copolyester derived from glycolide and at least one additional monomer selected from the group consisting of 1-lactide, trimethylene carbonate, [epsilon]-caprolactone, p-dioxanone, 1,5-dioxepan-2-one and a morpholinedione.

Another key aspect of this invention deals with multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles, wherein the absorbable multifilament yarn of the knitted mesh comprises a crystalline, high molecular weight segmented polyaxial copolyester exhibiting an inherent viscosity of from about 0.6 to about 2.3 dL/g and a heat of fusion ([Delta]Hf) of from about 30 to about 90 J/g, the copolyester derived from glycolide and at least one additional cyclic monomer of 1-lactide, trimethylene carbonate, [epsilon]-caprolactone, p-dioxanone, 1,5-dioxepan-2-one and a morpholinedione, and wherein the stent is packaged in a dry, hermetically sealed foil pack and is irradiated with from about 3 to about 35 kGy of high energy radiation. Alternatively, wherein the stent is packaged in a dry, hermetically sealed foil pack and is irradiated with from about 30 to about 40 kGy of gamma rays or electron beam radiation.

A technologically important aspect of this invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles and wherein the stent is packaged in a dry, hermetically sealed foil pack containing a formaldehyde-generating packet, and is irradiated with from about 3 to about 15 kGy of gamma rays or electron beam radiation.

A second general aspect of this invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, at least three absorbable strands overlying the coil and extending along the longitudinal axis of the stent, the strands comprising a copolyester derived from at least one monomer selected from the group consisting of 1-lactide, glycolide, trimethylene carbonate, [epsilon]-caprolactone, p-dioxanone, 1,5-dioxepan-2-one and a morpholinedione, wherein the stent exhibits a one- to ten-week, radiomodulated absorption/disintegration and strength retention profiles and wherein the absorbable strands are selected from the group consisting of monofilament yarn having a diameter between about 20 and about 150 microns, a 20-filament, 60 to 100 denier yarn, and a braided multifilament yarn having a diameter of from about 0.02 to about 0.2 mm.

A clinically important aspect of this invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles wherein said stent comprises at least one bioactive agent selected from the group consisting of antimicrobial, antiviral, antineoplastic, anti-anesthetic, anti-inflammatory, analgesic, and cell-growth promoting agents and wherein the at least one bioactive agent comprises an antimicrobial agent and wherein the antimicrobial agent comprises an antibacterial agent selected from the group consisting of triclosan, clindamycin, mitomycin, doxycycline, and metronidazole and further wherein the at least one bioactive agent comprises an antimicrobial agent and wherein the antimicrobial agent comprises antifungal agent selected from the group consisting of miconazole, fluconazole, and ketoconazole.

Another clinically important aspect of this invention deals with a multi-component absorbable/disintegratable, fiber-reinforced, radiopaque composite, non-migrating stent for a urinogenital conduit, the stent comprising a first component comprising an absorbable, highly compliant, hydrowettable, tubular matrix, the matrix reinforced with a load-bearing, radiopaque central coil, the coil comprising an absorbable polyester/inorganic radiopaque hybrid composition, the coil shrouded with a knitted mesh construction comprising an absorbable multifilament yarn, wherein the stent exhibits a one- to ten-week, radiomodulated absorption/disintegration and strength retention profiles wherein said stent comprises at least one bioactive agent selected from the group consisting of antimicrobial, antiviral, antineoplastic, anti-anesthetic, anti-inflammatory, analgesic, and cell-growth promoting agents and wherein the at least one bioactive agent comprises an antineoplastic agent and wherein the antineoplastic agent is selected from the group consisting of paclitaxel and 5-fluorouracil.

BRIEF DESCRIPTION OF THE DRAWINGS

The accompanying drawings, which are incorporated in and constitute a part of the specification, illustrate presently preferred embodiments of the present invention and, together with the general description give above and the detailed description of the preferred embodiments given below, serve to explain the principles of the present invention.

DETAILED DESCRIPTION OF PREFERRED EMBODIMENTS

An increasing geriatric population and associated health complications due to compromised functionality of different urinogenital conduits directed the attention of contemporary investigators to explore time-dependent corrective measures relying on the use of temporary devices made of absorbable/biodegradable polymers which can be formulated to be disintegratable and radiographically detectable. This also obviates the need for removal following the conclusion of their corrective functions. Typical applications of this clinical strategy were the subject of recent patent applications on absorbable and absorbable/disintegratable radiopaque endourological stents (U.S. application Ser. Nos. 11/346,117; 11/204,822; and 60/650,240). However, this prior art did not address patent-specific requirements, depending on age, type of urinogenital conduits (e.g., urethra, ureter, vas deferens, and fallopian tube), type of ailment and level of urgency and other factors, such as patient comfort during deployment of the device. Accordingly, this invention focuses on the use of (1) hydrophilic additives, such as polyethylene glycol and its copolymers, as well as acylated derivatives thereof, with the matrix polymer, to improve the device surface lubricity and hence patient comfort during deployment; (2) radiochemical sterilization using 3 to 15 kGy of gamma radiation or E-beam to achieve reproducible sterility while controlling the radiation dose to modulate the absorption/disintegration and strength loss profiles-the higher dose accelerates the rate of degradation and shortens the residence time at the biological site; (3) traditional high-energy radiation sterilization in the presence of dry air or nitrogen environments to achieve reproducible sterility and also to modulate the absorption/disintegration and strength loss profile by varying the radiation dose between 25 and 40 kGy, with or without changing the dose rate to accentuate the radiation effect (using gamma radiation or E-beam), particularly when the gas environment in the hermetically sealed package is dry air or nitrogen; and (4) a bioactive active agent, including triclosan, to reduce the incidence of infection at the biological site. Accordingly, the teaching of the present invention entails the proper inventive steps to address the aforementioned points.

Figure 1:
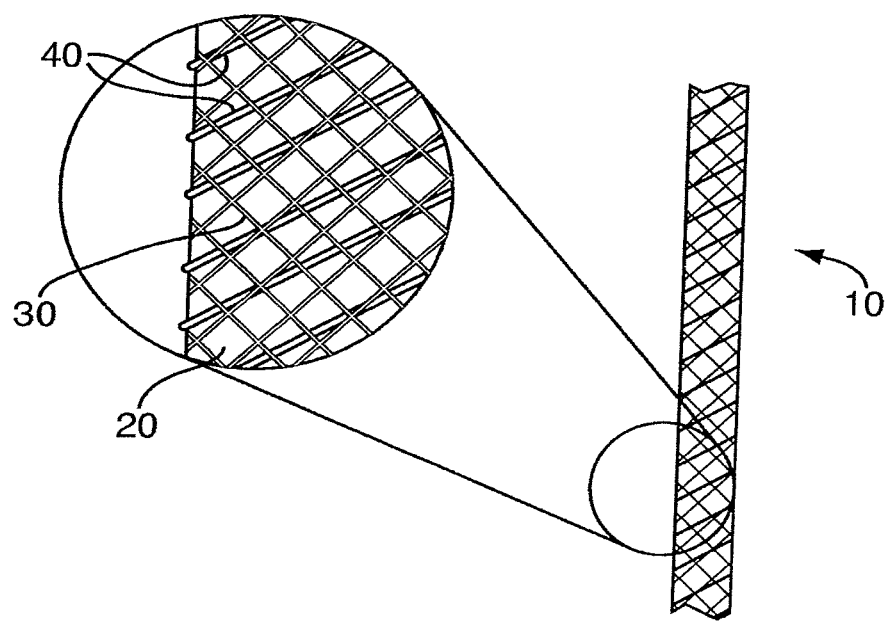
FIG. 1 is a side elevation view of an endoureteral stent in accordance with the present invention, in a planar configuration, with an exploded view of the fiber reinforcement.
Figure 2:
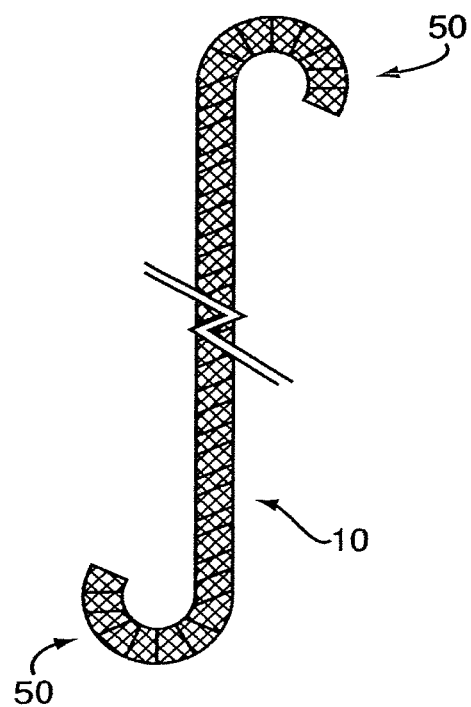
FIG. 2 is a side elevation view of the endoureteral stent of FIG. 1 depicting a position-retaining end.

As shown in FIG. 1, an embodiment of the stent is a construct 10 of a fiber reinforced matrix 20. The fiber-reinforcement is a coil 40. The coil 40 is shrouded in a mesh 30. Referring now to FIG. 2, an embodiment of the construct 10 further includes at least one position-retaining end 50.

Further illustrations of the present invention are provided by the following examples:

Example 1

Synthesis and Characteristics of Radiopaque, Triaxial, Segmented Glycolide Copolymer (MG5-B) for Use in Coil Production The reaction apparatus was comprised of a 1 L stainless steel kettle with a 3-neck glass lid equipped with an overhead mechanical stirring unit, vacuum adapter, and nitrogen inlet. After obtaining a vacuum <=0.5 mmHg, the apparatus was purged with nitrogen. The polymeric initiator, paxTMC-1, is a polytrimethylene carbonate (TMC) initiated by trimethylolpropane at a monomer to initiator ratio of 15. An initial charge of paxTMC-1 (9.15 g), predried at 220 [deg.] C. barium sulfate microparticles (245 g, diameter=1-4 [mu]m), glycolide (313.8 g, 2.7048 moles), and [epsilon]-caprolactone (132.1 g, 1.1592 moles) was added to the kettle. The apparatus was then lowered into an oil bath.

The apparatus and its contents were placed under vacuum at 40 [deg.] C. for 1 hour. The system was then purged with nitrogen. The temperature of the oil bath was increased to 95 [deg.] C. and the contents mixed thoroughly. Once mixed the final charge, a 0.2 M toluene solution of stannous octanoate (2.576 mL, 5.152*10<-4>moles) was added. The temperature of the oil bath was increased to 180 [deg.] C. and mixing was continued as long as possible, then the reaction was maintained at 180 [deg.] C. for 7 hours.

The polymer was frozen, removed and ground. The ground material was sieved. Polymer was transferred to a 2 L pear shaped glass flask and placed on a Buchi rotavapor. After obtaining a vacuum of 0.25 mmHg, the flask was lowered into an oil bath. The temperature was increased to 40 [deg.] C. After 2 hours at 40 [deg.] C., the temperature of the oil bath was increased to 80 [deg.] C. After 1 hour at 80 [deg.] C., the temperature was increased to 110 [deg.] C. Temperature was maintained at 110 [deg.] C. for 4 hours.

The inorganic content was determined using ASTM ash test to be between 38-40%. The inherent viscosity using Hexafluoroisopropanol as a solvent was about 0.95 dl/g. The melting temperature and heat of fusion, as determined by differential scanning calorimetry, were about 215 [deg.] C. and about 35 J/g, respectively.

Example 2

Melt-Spinning and Properties of Radiopaque Monofilaments Using MG5-B from Example 1 and Its Processing Into a Coiled Scaffold (CS)

A single screw extruder with four zones was used to extrude the polymer into monofilament. The polymer from Example 1 was extruded using a 0.6 mm die. A 325 line per inch filter pack was used. Zone 1 was maintained at 100 [deg.] C. Zone 2 was maintained at 175 [deg.] C. Zone 3 was maintained at 212 [deg.] C. Zone 4/Spin Pack were maintained at 214 [deg.] C. The metering pump was operated at 8 rpm while the take up roll was set at 40-60 rpm. The collected monofilament had diameters between 0.58 mm and 0.61 mm. The fiber was drawn at 4.5* in the first stage at 55 [deg.] C. and 0.5* in the second stage at 70 [deg.] C. resulting in a diameter of 0.30 mm to 0.33 mm. The free shrinkage was 8.85% to 10.43% at 50 [deg.] C. The fiber was relaxed one half the free shrinkage plus 2% at 70 [deg.] C. The resulting fiber had a maximum load of about 13 N and was dimensionally stable.

The processed radiopaque monofilament was then coiled in a helical manner onto a 0.55" diameter Teflon cord which maintained the inner diameter of the scaffold. The material was applied using a custom device, placing 33 to 35 coils per inch.

Example 3

Synthesis and Characterization of a Triaxial, Segmented Glycolide Copolymer (MG-9) For Use in Preparing Knitted Scaffolds The reaction apparatus was comprised of a 1 L stainless steel kettle with a 3-neck glass lid equipped with an overhead mechanical stirring unit, vacuum adapter, and nitrogen inlet. After obtaining a vacuum of 0.5 mmHg, the apparatus was purged with nitrogen. An initial charge of paxTMC-1 (16.0 g), as mentioned in Example 1, [epsilon]-caprolactone (38.6 g, 0.3382 moles), and Glycolide (745.4 g, 6.4262 moles) was added to the kettle. The apparatus was then lowered into an oil bath.

The kettle and the contents are heated to 110 [deg.] C. and mixed under positive nitrogen pressure. Once the polymeric initiator appears to be thoroughly dissolved into the monomer, a 0.2 M toluene solution of stannous octanoate (0.966 ml, 1.933*10<-4>moles) was added. The temperature is increased to 180 [deg.] C. Stirring is stopped when polymer mixture gets viscous. The reaction is maintained at 180 [deg.] C. for 5 hours.

The polymer was frozen, removed and ground. The ground material was sieved. Polymer was transferred to a 2 L pear shaped glass flask and placed on a Buchi rotavapor. After obtaining a vacuum of 0.5 mmHg, the flask was lowered into an oil bath. The temperature was increased to 40 [deg.] C. After 2 hours at 40 [deg.] C., the temperature of the oil bath was increased to 80 [deg.] C. After 1 hour at 80 [deg.] C., the temperature was increased to 110 [deg.] C. Temperature was maintained at 110 [deg.] C. for 4 hours.

The inherent viscosity using Hexafluoroisopropanol as a solvent was about 1.3 dl/g. The melting temperature, as determined by differential scanning calorimetry, was about 218 [deg.] C.

Example 4

Melt-spinning and Properties of Multifilament Yarn Using MG-9 from Example 3 and Its Processing to a Knitted Scaffold (KS)

A single screw extruder with five zones was used to extrude the polymer into multifilament. The polymer from Example 3 was extruded using a 20 hole die with 0.018" diameter holes. A 400 line per inch filter pack was used. Zone 1 was maintained at 190 [deg.] C. Zone 2 was maintained at 210 [deg.] C. Zone 3 was maintained at 222 [deg.] C. Zone 4/Pump was maintained at 228 [deg.] C. Zone 5/Spin Pack were maintained at 228 [deg.] C. The 0.584 cc/rev Zenith metering pump was operated at 6.0 rpm while the denier control roll was set to a linear speed of 315 meters/minute. The fiber was then oriented over three high speed godets traveling at 320, 465, 480 M/min. and heated to 60, 80, 26 [deg.] C. respectively. The collected multifilament was then reoriented at speeds of 250 M/min to 280 M/min, and at a temperature of 100 [deg.] C. The resulting fiber had a tenacity of 3.26 and a denier of 80.4.

The processed multifilament was then plied once to generate a 40 filament fiber and then weft knitted using a lamb circular knitter onto the coiled scaffold from Example 2 in a continuous manner. A [⅞]" knitting cylinder with 12 course gauge needles was used to form the knitted scaffold over the coiled scaffold.

Example 5

Synthesis and Characterization of a Triaxial, Segmented 1-Lactide Copolymer (SVG-12) For Use as a Reinforced Composite Matrix (CM)

The reaction apparatus was comprised of a 4 L stainless steel reactor equipped with an overhead mechanical stirring unit, vacuum adapter, and nitrogen inlet. After obtaining a vacuum <=0.5 mmHg, the apparatus was purge with nitrogen. Oil is heated and circulated through the jacketed reactor to control the temperature. An initial charge of glycolide (254.9 g, 2.1976 moles), trimethylene carbonate (348.7 g, 3.4185 moles), predried triethanolamine (3.0319 g, 2.0348*10<-2>moles), stannous octanoate (354.5 mg, 8.752*10<-4>moles), and [epsilon]-caprolactone (974.3 g, 8.5463 moles) was added a 2 L flask and dried under high vacuum for 1.25 hours at 40 [deg.] C. The flask was then added to the 4 L reactor.

The system was then purged with nitrogen. The temperature of the oil was increased to 175 [deg.] C. and the contents mixed thoroughly for 6.5 hours and then the temperature was reduced. Once mixed, the final charge, of glycolide (226.6 g, 1.9534 moles) and 1-Lactide (1195.5 g, 8.3021 moles) was added. The temperature of the oil was then increased to 135 [deg.] C. and maintained for 19 hours.

The polymer was then removed and dissolved at a concentration of 4 milliliters per 1 gram in dichloromethane (DCM) so that the polymer can be precipitated out in −60 [deg.] C. isopropyl alcohol (IPA) and any monomer will stay dissolved and be rinsed away. The polymer is then allowed to dry to a constant weight.

The inherent viscosity using Chloroform as a solvent was about 1.4 dl/g. The melting temperature and heat of fusion, as determined by differential scanning calorimetry, were about 110 [deg.] C. and about 7.2, respectively. The Mn and Mw were determined by GPC in dichloromethane (Mn=85 kDa and Mw=146 kDa).

Example 6

Assembling a Typical Composite Ureteral Stent Construct

Preparation of polymer matrix solution-A polymer solution containing SVG-12 from Example 5, polyethylene glycol (MW=4600) and acetone was prepared by addition of 1600 milliliters of acetone to one 64-ounce jar, followed by addition of 16.0 grams of PEG 4600 and 144.0 grams of purified SVG-12. The solution was enclosed and brief heating was used to facilitate dissolution. The jar was placed on automatic rolling apparatus until complete dissolution was reached.

Continuous impregnating of knitted core-The dry, knitted core was impregnated with a polymer matrix of SVG-12 and PEG 4600 using a continuous matrix-impregnating process that involved the continuous movement of the knitted core material through a 0.75-liter bath of polymer solution. The knitted core was unspooled from the beginning of the impregnating apparatus and immediately fed into the bath of polymer solution, where two in-line submerged pulleys kept the scaffold material submerged for the length of the bath. As the impregnated material exited the bath, it was passed through an air-circulating drying tube heated to 40 [deg.] C., then a stainless-steel element heated to 50 [deg.] C., and then the impregnated material was spooling onto a final take-up spool.

Shape-forming of impregnated, knitted core-The impregnated material was wrapped onto custom-built racks equipped with two parallel stainless steel bars of 0.5 inch diameter, which could be adjusted for separation distance to control final stent length. The newly-impregnated, knitted core was wrapped onto these racks in a continuous fashion. The racks were annealed at 130 [deg.] C. for 30 minutes, and then the racks were allowed to cool to room temperature in a laminar flow hood. Multiple stents were removed from each rack by cutting the scaffolding material at appropriate positions along interior positions of the separation rods of the shape-forming racks. These stents, which still contained a Teflon core, were modified by addition of a UVJ marker to each stent stem within one centimeter of what would ultimately become the proximal loop of each stent. Then, the proximal loops of all stents were given an additional coating by hand-dipping each proximal loop into 150 milliliters of a 10% (w/v; 9.3% SVG-12, 0.7% PEG 4600) polymer solution of SVG-12 and PEG 4600 in acetone. Stents were hung by distal loops in a laminar flow hood to dry. Then, Teflon cores were removed from each stent by securing one end of the Teflon to position-fixed vise-grip pliers as the opposite end of the Teflon was stretched using a second set of vise-grip pliers. A clean cut was made in the stretched Teflon core at the secured end, and then the Teflon core of reduced diameter was pulled through the stent and discarded. Finally, each stent was trimmed to the appropriate specifications.

Example 7

Package Design and Packaging of UST from Example 6

The UST, as described in Example 6, is packaged in a tray that was made of a polyester suitable for use in radiation sterilization. A liner that fits in the tray has tabs that retain the stent in location. The tray has a top and bottom section with closure devices on both ends and provided protection to the stent during shipping and storage. The tray is also placed in a foil pouch, which provided moisture barrier, to protect the UST.

Example 8

Radiation Sterilization of UST from Example 6 and Evaluation of the Sterile Device Properties Sterilization of the UST from Example 6, package as described in Example 7 was conducted using 25 KGy of gamma radiation.

The melting temperature, as determined by differential scanning calorimetry, were 52-62, 114-144, 198-208, and 206-216 [deg.] C., respectively. The functionality of the stent was determined through mechanical testing. This entails: (1) determining the axial compression (to ensure the stent is insertable with traditional placement techniques) which was found to be about 4 N; (2) determining the radial compression for a 1" section of the stent which was found to be about 94 N; (3) measuring the curl retention which was found to be about 0.5 N; and (4) measuring the total yield strength of the stent which revealed a value of about 93 N. Mass loss after one week in vitro at pH 7.2 and 37 [deg.] C. was found to be 3.3% for the non-sterilized stent and 6.3% for the Gamma sterilized stent.

Example 9

Preparation and Properties of an Antimicrobial Endoureteral Stent (A-UST)

Preparation of a polymer matrix solution of Example 6 was adjusted to include triclosan at a concentration of 0.5% or 1% of the solid polymer weight. Antimicrobial susceptibility testing demonstrated that the Uriprene stent provided a sustained drug release and displayed a significant inhibitory effect on *S. aureus* for at least 8 days.

What is claimed is:

1. A multi-component, absorbable, fiber-reinforced, radiopaque, tubular stent for a urinogenital conduit comprising:
   i) a central coil comprising an absorbable radiopaque hybrid composition comprising radiopaque particles dispersed in a crystalline polyaxial copolyester, the copolyester derived from glycolide and at least one additional monomer selected from the group consisting of l-lactide, trimethylene carbonate, ε-caprolactone, p-dioxanone, 1,5-dioxepan-2-one, and a morpholinedione;
   ii) a tubular knitted mesh disposed on one surface of the central coil, the coil and the knitted mesh together forming a knitted core, the knitted mesh comprising an absorbable polymeric multifilament yarn comprising a crystalline polyaxial copolyester, the copolyester derived from glycolide and at least one additional monomer selected from the group consisting of l-lactide, trimethylene carbonate, ε-caprolactone, p-dioxanone, 1,5-dioxepan-2-one, and a morpholinedione;
   iii) a composite matrix, the matrix being of a composition comprising an absorbable polyaxial copolyester and a hydrophilic polymer additive, the copolyester derived from 1-lactide and at least one additional monomer selected from the group consisting of glycolide, trimethylene carbonate, ε-caprolactone, p-dioxanone, 1,5-dioxepan-2-one, and a morpholinedione, said composite matrix reinforced with and impregnating the knitted core such that the composite matrix forms a tube,
      wherein the hydrophilic polymeric additive has a molecular weight of 1 to 70 kDa, the hydrophilic polymeric additive selected from the group consisting of polyethylene glycol, and polyethylene glycol endgrafted with at least one monomer selected from the group consisting of l-lactide, glycolide, trimethylene carbonate, e-caprolactone, p-dioxanone, 1,5-dioxepan-2-one and a morpholinedione,
      wherein the matrix and knitted core alone are capable of maintaining patency of a urinogenital conduit.

2. A multi-component, absorbable, fiber-reinforced, radiopaque, tubular stent for a urinogenital conduit as set forth in claim 1, wherein the copolyester of the matrix exhibits an inherent viscosity of from 0.5 to 2.0 dL/g and heat of fusion (ΔHf) of from 2 to 30 J/g.

3. A multi-component, absorbable, fiber-reinforced, radiopaque, tubular stent for a urinogenital conduit as set forth in claim 1 wherein the copolyester of the yarn of the knitted mesh exhibits an inherent viscosity of from 0.6 to 2.3 dL/g and a heat of fusion (ΔHf) of from 30 to 90 J/g.

* * * * *